(12) United States Patent
Longoni et al.

(10) Patent No.: US 9,649,380 B2
(45) Date of Patent: May 16, 2017

(54) COMPOSITIONS COMPRISING PROBIOTIC AND PREBIOTIC COMPONENTS AND MINERAL SALTS, WITH LACTOFERRIN

(75) Inventors: Valeria Longoni, Latina (IT); Marisa Penci, Latina (IT)

(73) Assignee: Pfizer Italia S.R.L. (IT)

( * ) Notice: Subject to any disclaimer, the term of this patent is extended or adjusted under 35 U.S.C. 154(b) by 0 days.

(21) Appl. No.: 13/179,712

(22) Filed: Jul. 11, 2011
(Under 37 CFR 1.47)

(65) Prior Publication Data
US 2012/0207712 A1    Aug. 16, 2012

(30) Foreign Application Priority Data

Jan. 12, 2009   (IT) .............................. MI2009A0019

(51) Int. Cl.
| | | |
|---|---|---|
| A61K 35/74 | (2015.01) | |
| A61K 47/02 | (2006.01) | |
| A61K 35/745 | (2015.01) | |
| A61K 35/747 | (2015.01) | |
| A61K 38/06 | (2006.01) | |
| A61K 38/40 | (2006.01) | |
| A61K 47/18 | (2017.01) | |
| A61K 9/00 | (2006.01) | |
| A61K 47/26 | (2006.01) | |
| A61K 47/42 | (2017.01) | |
| A23L 33/135 | (2016.01) | |
| A23L 33/16 | (2016.01) | |
| A23L 33/19 | (2016.01) | |
| A23L 33/21 | (2016.01) | |

(52) U.S. Cl.
CPC ............ *A61K 47/02* (2013.01); *A23L 33/135* (2016.08); *A23L 33/16* (2016.08); *A23L 33/19* (2016.08); *A23L 33/21* (2016.08); *A61K 9/0095* (2013.01); *A61K 35/745* (2013.01); *A61K 35/747* (2013.01); *A61K 38/063* (2013.01); *A61K 38/40* (2013.01); *A61K 47/183* (2013.01); *A61K 47/26* (2013.01); *A61K 47/42* (2013.01)

(58) Field of Classification Search
CPC . C12N 1/16; C12N 1/20; A61K 36/06; A61K 35/74; A61K 35/741; A61K 35/744; A61K 35/745; A61K 35/747
See application file for complete search history.

(56) References Cited

U.S. PATENT DOCUMENTS

| | | | |
|---|---|---|---|
| 6,241,983 B1 | 6/2001 | Paul et al. | |
| 2004/0223956 A1 | 11/2004 | Naidu et al. | |
| 2006/0093592 A1* | 5/2006 | Cheruvanky et al. | 424/93.45 |
| 2007/0292402 A1* | 12/2007 | Pirovano et al. | 424/93.45 |
| 2008/0241226 A1* | 10/2008 | Abeln et al. | 424/439 |
| 2008/0274085 A1* | 11/2008 | Daube et al. | 424/93.4 |

FOREIGN PATENT DOCUMENTS

| | | |
|---|---|---|
| EP | 1917969 A1 * | 5/2008 |
| WO | WO2004/028460 A2 | 11/2004 |

OTHER PUBLICATIONS

AOR (Advanced Biotics, AOR, 2007, available at http://www.cureself.com/research/NPA-Advanced-Biotics.pdf, screen capture indicating file has been available since Jul. 8, 2007 also provided).*
AcidophilusUltra, New Roots Herbal, 2008, available at http://www.newrootsherbal.com/uploads/downloads/pdf/english/AcidophilusUltra.pdf, screen capture indicating file available since Oct. 6, 2008 also provided.*
Tallarida, Ronald, "Drug Synergism and Dose-Effect Data Analysis", Chapman and Hall/CRC, Boca Raton Fl, Chapter 1 and Chapter 4, (2000).*
Berenbaum M, "What is Synergy" Pharmacological Reviews, vol. 1989, No. 41, (1989) pp. 93-141.*
Berenbaum M, "Synergy, additivism and antagonism in immunosuppression" Clinical Experimental Immunology (1977), vol. 28 pp. 1-18.*
De Bortoli et al: "Helicobacter pylon eradication: a randomized prospective study of triple therapy versus triple therapy plus lactoferrin and probiotics." The American Journal of Gastroenterology, May 2007, vol. 102, No. 5, pp. 951-956.
Nicar Laboratoies Inc "Probaclac" May 12, 2008, Retrieved from the internet: URL:http//web.archive.org/web/20080512083340/http://www.nicar.ca/engprod_probaclac.html.
St. Justin's Hospital: "Randomized Controlled Trial of Probaclac Versus Placebo in Children Aged8 to 18 Years with Irritable Bowel Syndrom" ClinicalTrials.gov, Nov. 18, 2008, URL: http//clinicaltrials.gov/archive/NCT00793494/2008_11_18.
Niers Laetitia et al: "Nutritional support for the infant's immune system." Nutrition Reviews, vol. 65, No. 8 Pt.1, Aug. 2007, pp. 347-360.
Coppa et al "Prebiotics in human milk: a review." Digestive and Liver Disease, W.B. Saunders, vol. 28, Dec. 1, 2006, pp. S291-S294.
Diop et al: "Probiotic food supplement reduces stress-induced gastrointestinal symptoms in volunteers: a double-blind, placebo-controlled, randomized trial." Nutrition Research, Elsevier Inc., vol. 28, No. 1, Jan. 15, 2008, pp. 1-5.
D'Souza A L et al: "Probiotics in prevention of antibiotic associated diarrhea: Meta-analysis," British Medical Journal 20020608 GB, vol. 324, No. 7350, Jun. 8, 2002, pp. 1361-1364.

(Continued)

*Primary Examiner* — Robert Yamasaki
*Assistant Examiner* — Charles Zoltan Constantine
(74) *Attorney, Agent, or Firm* — Maureen P. O'Brien; Jeffrey M. Gold

(57) ABSTRACT

The present invention relates to compositions comprising probiotic and prebiotic components, mineral salts, lactoferrin, and possibly saccharomycetes, which perform correct, effective colonisation of the probiotic components administered, with enteric consequences which involve maintaining and/or restoring intestinal health and preventing the consequences of common dysbioses of the digestive tract caused by stress, incorrect dietary habits and antibiotic treatments. Said compositions also have a concomitant anti-inflammatory and immunomodulating action.

2 Claims, No Drawings

(56) References Cited

OTHER PUBLICATIONS

Timmerman H M et al: "Monostrain, multistrain and multispecies probiotics—A comparison of functionality and efficacy." International Journal of Food Microbiology, Elsevier Science Publishers, Amsterdam, NL, vol. 96, No. 3, Nov. 15, 2004. pp. 219-233.
Williams E A et al: "Clinical trial: a multistrain probiotic preparation significantly reduces symptoms of irritable bowel syndrome in a double-blind placebo-controlled study." Alimentary Pharmacology & Therapeutics, vol. 29, No. 1, Sep. 9, 2008, pp. 97-103.
King et al: "Oral Solid Dosage Forms," Remington's Pharmaceutical Handbook, Mack Publishing Co., NY, USA, 17th Ed., 1985, pp. 1603-1832.

\* cited by examiner

US 9,649,380 B2

COMPOSITIONS COMPRISING PROBIOTIC AND PREBIOTIC COMPONENTS AND MINERAL SALTS, WITH LACTOFERRIN

CROSS REFERENCE TO RELATED APPLICATION

This application is a continuation-in-part of International Patent Application No. PCT/US2010/020712, filed Jan. 12, 2010 and claims the benefit from Italian Patent Application No. MI2009A000019, filed Jan. 12, 2009. The content of this application is incorporated herein by reference in its entirety.

FIELD OF THE INVENTION

The present invention relates to compositions comprising a probiotic, more specifically *Bifidobacterium longum*, and a carrier material comprising prebiotic materials, mineral salts, and lactoferrin will not only have improved and/or enhanced survival of the probiotic species, but also performs effective colonization of the probiotic components administered with enteric consequences of common dysybioses of the digestive tract caused by stress, incorrect dietary habits, antibiotic treatments, illness and the like. Said compositions also have a concomitant anti-inflammatory and immuno-modulating action. Additionally, the invention is directed to methods for enhancing and/or improving the survival and viability of a probiotic organism with the compositions described herein.

The compositions of the present invention can be used for the preparation of nutritional supplements and pharmaceutical-grade products.

BACKGROUND OF THE INVENTION

Consumers are becoming increasingly aware of matters which may be necessary for maintenance of their environment, health and nutrition. In response, scientific research has focused upon the roles that diet, stress, and modern medical practices (e.g. antibiotics and radiotherapy) may play in threatening human health. In particular, population dynamics shifting towards older societies are increasing the incidence of illnesses which may be caused by deficient or compromised microflora such as gastrointestinal tract (GIT) infections, constipation, irritable bowel syndrome (IBS), inflammatory bowel disease (IBD)—Crohn's disease and ulcerative colitis, food allergies, antibiotic-induced diarrhea, cardiovascular disease, and certain cancers (e.g. colorectal cancer).

In recent years the commercial manufacture and marketing of functional foods (foods which affect functions of the body in a targeted manner so as to bring about positive affects on physiology and nutrition), particularly probiotic containing foods, has spread from the well-established Japanese niche market place into the global marketplace. While a number of probiotic bacteria of human origin are now being exploited commercially the science is still emerging not only regarding potential applications of such products but also on how to improve the efficacy as well.

Probiotics have been defined as live microbial food supplements which beneficially affect the host by improving the intestinal microbial balance, or more broadly, as living micro-organisms, which upon ingestion in certain numbers, exert health effects beyond inherent basic nutrition. Cocktails of various micro-organisms, particularly species of *Lactobacillus* and *Bifidobacterium*, have traditionally been used in fermented dairy products to promote health. However to be effective, said probiotics must not only survive manufacturing processing, packaging and storage conditions, but also then must survive transit through the gastro-intestinal tract so the probiotic material remains viable to have a positive health effect.

The evolutionary history of man has been influenced by bacteria, not only as regards epidemics. A less evident and more submerged influence is that of commensal flora, especially the one resident in the human intestine, which perform a major "protective" and "educational" role (the first role is performed on the whole body, and the second on its immune system), and constantly defend the individual against disease. As is indeed well-known, under normal conditions, the skin and much of the mucous membranes of the body are "inhabited" by a varied flora of micro-organisms, which are often tissue-specific. For example, the predominant micro-organisms in the intestine (no less than 500 strains have been identified to date), especially in the large intestine, are *Bacteroides* spp., *Clostridium* spp, *Fusobacterium* spp *Klebsiella* spp., *Staphylococci,* yeasts and *Escherichia coli*. This commensal microbial flora can be divided into two categories: "resident" flora, which is nearly always present and, if altered, can be rapidly restored; and "transient" flora, which can colonise in the host for short periods, due to the lack of ability of transient flora to compete with the resident micro-organisms or the host's defence mechanisms. Transient flora sometimes also includes potentially pathogenic micro-organisms. The exact composition of the flora is influenced by factors of microbial origin and factors specific to the host. However, as these latter factors (age, nutritional level, hormones and disease) are difficult to modify, the analysis will focus on the former.

An important microbial factor which influences the composition of the commensal flora is the ability of bacteria to adhere to the epithelial cells. Some bacteria present marked tropism (affinity) for particular epithelial cells. The normal flora can then interfere with the potentially pathogenic micro-organisms by competing with them for the receptors on the cell surface. Commensal flora can also interfere with pathogenic micro-organisms by producing bacteriocins, substances which inhibit the growth of other bacteria (usually of the same species), or by providing an acidic environment through the production of short chain fatty acids or by competing for the same nutrients. Other useful mechanisms are the stimulus to produce natural antibodies with cross-reactivity, or stimulation of clearance mechanisms. However, the latter are much less important.

Due to these mechanisms, the normal flora forms an effective barrier against colonisation of the host's surfaces by pathogenic micro-organisms. This is known as "colonisation resistance".

As may thus be easily inferred, any phenomenon that reduces the effect of these microbial factors on the gastroenteric ecosystem can lead to serious problems for the health of the individual. For example, treatment with broad-spectrum antibiotics eliminates all the commensal bacteria of the gastroenteric flora which are sensitive to the antimicrobial agent used. In this case, colonisation resistance is reduced, and potentially lethal micro-organisms are free to colonise the mucosa. When the treatment is discontinued, the resident flora can be restored, obviously, with time. Unfortunately, however, aerobic Gram-negative bacteria grow faster and colonise the mucous membranes sooner than anaerobic Gram-negative bacteria, which proliferate more slowly, although they constitute 99% of the commensal flora. In patients whose immune defences are even only partly impaired, this imbalance can cause Gram-negative bacteraemia.

Other possible consequences associated with suppression of the normal flora by broad-spectrum antibiotics include excessive growth of yeasts with the appearance of mycosis, or excessive growth of the anaerobic Gram-negative bacterium *Clostridium difficile*, which is unfortunately relatively antibiotic-resistant. Its presence can lead to a series of very common disorders, ranging from diarrhea to colitis.

The immune system and its functions are the result of thousands of years of development, determined day after day by constant interaction with the world of the microorganisms, especially at gastrointestinal level.

It has been scientifically proved that aseptic conditions obtained with excessive hygiene or excessive use of antibiotics does not represent a successful strategy in terms of individual health, especially in view of the excellent conditions of present-day life (compared with the recent past). The damage which even partially aseptic conditions can cause is well known, namely food intolerances, allergies and autoimmune diseases. These problems result from lack of contact between the commensal flora and the immune system. Through this everyday contact, the commensal flora teaches the immune system how to distinguish between "self" and "non-self". A great deal of epidemiological evidence (and experimental tests conducted, for example, with germ-free animals) proves this theory.

A significant increase in the rate of food intolerances and allergies (up 40%), and autoimmune disorders (up 30%) such as multiple sclerosis, lupus erythematosus and rheumatoid arthritis, has been observed in the economically developed countries since the Fifties and Sixties, in parallel with the reduction in mortality from infectious diseases (due to the availability of more and more antibiotics). These increases are the result of a substantial change in the quality and amount of gastro-enteric commensal flora due to incorrect use of antibiotics and an increasingly stressful lifestyle and also, in the case of infants, to a reduction in breastfeeding. Indeed, it has often been reported that breastfed children suffer from fewer food intolerances and allergies than children who receive so-called "artificial" milk. Even more recently, the same correlation was reported for multiple sclerosis (an autoimmune disease). Conversely, analysis of the morbidity of individuals who live in tribal environments (in parts of Africa, India or inland Australia) where the lifestyle is primordial shows an almost total absence of diseases like allergies and autoimmunity (although there is obviously a high rate of infectious disease).

Antibiotic treatment, stress and lack of breastfeeding, which alter the quality and amount of the gastroenteric commensal flora, reduce the chance that the commensal flora will come into contact with the immune system. As a result of this contact, the cells of the immune system, especially type 1 and 2 T-helper lymphocytes, are "taught" to tolerate (ie. not to respond to) food antigens and innocuous non-food antigens (such as pollens), or the proteins of the body to which they belong (thus preventing autoimmune diseases).

The exceptional importance of commensal flora for the present and future health of each individual is therefore evident. However, humans are not born with commensal flora. On the contrary, at birth, the gastroenteric tract is sterile. Its colonisation is initiated at the moment of birth by the mother's vaginal and anal flora, in the case of a vaginal birth or by exposure to the environment outside of the womb in the case of a caesarean delivery and in both cases is subsequently influenced by the type of milk given and by maternal/environmental factors. After the neonatal stage, the gastroenteric commensal flora of a healthy individual consists of at least $10^{18}$ bacteria, 99% of which belong to some 30-40 species.

This flora therefore consists of anaerobic germs (bifidobacteria, clostridia, bacterioids, eubacteria and Gram-positive cocci) and aerobic germs (lactobacilli, streptococci, staphylococci and coliforms). However, these amounts are not equally distributed along the gastroenteric axis: the bacteria content is relatively low in the stomach (under 1 million per gram), but the amount increases substantially in the ileum (100 million) and enormously in the colon (100 billion).

Therefore there exists a need in the art for compositions that contain probiotic materials that not only survive the manufacturing processing conditions but that then can survive the gastrointestinal tract thereby delivering viable probiotic materials to the host in need thereof.

SUMMARY OF THE INVENTION

In its broadest aspect, the present invention provides for a probiotic compositions comprising: a) one or more probiotic components, comprising *Bifidobacterium longum* and at least one species of bacteria selected from the group of bacteria consisting of *Lactobacillus rhamnosus, Lactobacillus helveticus* and *Lactobacillus plantarum;* and b) a carrier composition comprising: 1) one or more prebiotic components; 2) lactoferrin; 3) one or more mineral salts; and optionally 4) glutathione.

In a first aspect of the invention, it is preferred that that the *Bifidobacterium longum* is *Bifidobacterium longum* R175 ("Rosell 175"), that the *Lactobacillus helveticus* is *Lactobacillus helveticus* R52 ("Rosell 52"); that the *Lactobacillus rhamnosus* is *Lactobacillus rhamnosus* R11 ("Rosell 11"), and that the *Lactobacillus plantarum* is *Lactobacillus plantarum* R1012 ("Rosell 1012"). *Lactobacillus helveticus* Rosell 52 is also known in the industry as a *Lactobacillus acidophilus* species and therefore as used herein, *Lactobacillus helveticus* R52 may also be known as *Lactobacillus acidophilus* R52.

In a preferred embodiment, the one or more prebiotic components are inulin and fructose. In another preferred embodiment, the one or more mineral salts is selected from the group consisting of zinc, magnesium, potassium and copper. In a most preferred embodiment the mineral salts comprise zinc gluconate, magnesium gluconate and potassium citrate.

An aspect of the invention provides for a probiotic composition comprising: a) a mixture of probiotic components comprising *Bifidobacterium longum* 50 billion CFU/g; *Lactobacillus helveticus* 150 billion CFU/g; and *Lactobacillus plantarum* 150 billion CFU/g; and b) a carrier comprising: 1) a mixture of prebiotics comprising about 80% of the total carrier composition; 2) lactoferrin in an amount of about 0 to about 10% of the total carrier composition; 3) mineral salts selected from the group consisting of magnesium, potassium and zinc salts, wherein magnesium is present in the carrier composition in an amount of about 0 to about 100%; wherein the potassium is present in an amount of about 0 to about 100% of the carrier composition; and wherein the zinc is present in an amount of about 0 to about 100% of the carrier composition; and 4) glutathione, wherein the glutathione in an amount of about 0 to about 20% of the carrier composition.

In yet another aspect of the invention, it is provided a probiotic composition a) a mixture of probiotic components consisting of *Bifidobacterium longum* R175 and *Lactobacillus rhamnosus* R11; b) a prebiotic component comprising inulin and fructose; c) lactoferrin; d) a mixture of mineral salts consisting of magnesium and zinc salts; and e) *Saccharomyces boulardii*.

In yet a further aspect of the invention is provided methods of use of probiotic containing compositions for the preparation of formulations for oral administration for the maintenance and/or restoration of intestinal health and for preventing dysbioses of any aetiology in mammals.

In yet a further aspect of the invention is provided for a method of improving the survivability of *Bifidobacterium longum* bacteria comprising: mixing the *Bifidobacterium longum* with *Lactobacillus helveticus* R52 and *Lactobacillus plantarum* R1012, wherein the survival of the *Bifidobacterium* is improved.

DETAILED DESCRIPTION OF THE INVENTION

In adults, antibiotic treatment, stress, dietary imbalances and disease (especially gastroenteric disorders) alter the quality and amount of the beneficial commensal flora. The problem of achieving a fast, efficient recolonisation process consequently arises. This process is significantly facilitated by probiotics.

It has now been found that a combination of a specific mixture of probiotic components, more specifically *Bifidobacterium longum*, when mixed in a carrier comprising (A) one or more prebiotic components, (B) lactoferrin, and (C) one or more mineral salts, and optionally saccharomycetes, has improved survival of the *Bifidobacterium longum* species as well as performs a considerable health-improving action, maintains and/or restores the intestinal health, manages the consequences of stress, and performs an anti-inflammatory and immunomodulating activity. More specifically, the compositions of the invention exhibit enhanced and/or improved survival of the probiotic components upon transit through the gastrointestinal tract.

The compositions according to the invention are therefore characterised by a considerable symbiotic value (probiotic with supported prebiosis), with a strong anti-inflammatory and immunomodulating component, and are also able to deal with changes in the fluid-salt balance. They consequently markedly improve/restore the intestinal health, and also have favourable repercussions in preventing malaise, infections and all the consequences of stress in general (especially physical and environmental stress).

Even though it has been shown that, at least for some probiotic strains, dead probiotics can elicit a clinical benefit, the clinical outcome in humans for dead bacteria is not as robust as for the viable cells. Therefore, in order to produce a probiotic product that is capable of eliciting the desired clinical effect, it is necessary to ensure that the probiotic containing composition has the highest percent cumulative survival of probiotics as they transit the upper gastrointestinal tract.

The inventors have found that combining *Bifidobacterium longum*, alone or in combination with one or more probiotic components, such as *Lactobacillus helveticus*, and/or *Lactobacillus plantarum* with a carrier comprising prebiotic preferably inulin, fructose and/or FOS; mineral salts comprising magnesium, zinc and/or potassium; lactoferrin; the *Bifidobacterium longum* has increased survival through the digestive tract and therefore the compositions exhibit greater efficacy.

Probiotics are traditionally defined as a nutritional supplement containing (preferably) live microbes which favourably influence the health of the host by improving the microbiological balance. Probiotic organisms must also be:
  normal components of the human intestinal flora or in any case readily adaptable to that habitat;
  able to cross the gastric barrier, withstanding the action of the bile acids and pancreatic enzymes;
  capable of specific adherence to the intestinal epithelium;
  easy to use in clinical practice.

The following probiotic bacteria meet the above definition:
  lactic-acid-producing bacteria in general;
  lactobacilli (*acidophilus, helveticus, bulgaricus, plantarum, casei, rhamnosus, lactis* and *reuteri*);
  *Streptococcus thermophilus*;
  *Enterococcus faecium*;
  *Bifidobacterium bifidum* and *longum*.

The mixture of probiotic components according to this invention comprises at least two species of bacteria selected from the group of bacteria consisting of:
  *Bifidobacterium longum*
  *Lactobacillus helveticus*
  *Lactobacillus acidophilus*
  *Lactobacillus rhamnosus*, and
  *Lactobacillus plantarum*.

In a preferred embodiment of the invention, the probiotic compositions comprise *Bifidobacterium longum*.

These live and vital microbial agents are capable of rapid colonisation, which soon leads to performance of their functions:
  1) protection by means of direct antagonism towards potentially pathogenic populations (inhibition of adherence to the epithelium; production of bacteriocins; competition for nutrients and substrates; creation of unfavourable pH conditions and redox microenvironments);
  2) stimulation and teaching of the immune system (macrophagic activation, boosting of natural killer cells, increased production of interferons, and balancing of T-helper 1 and 2 populations).
  3) acidification of the colonic environment by releasing lactate, propionate and butyrate.

The scientific community has recently focused its interest on the study and characterisation of those strains which seem to be the best candidates for the development of symbiotics (products containing both probiotics and prebiotics), namely lactobacilli (*acidophilus, helveticus, plantarum* and *rhamnosus*) and bifidobacteria. These different strains exhibit a variety of properties: ability to cross the gastric and bile barrier effectively; improvement of constipation and symptoms associated with lactose intolerance; attenuation of diarrhea (including types with a viral aetiology); production of bacteriocins; ability to inhibit pathogens such as *Salmonella, Shigella, Yersinia, Candida* and *Coli*; immunomodulation, and many others.

The genus *Lactobacillus* belongs to the group of lactic acid bacteria, which are Gram-positive prokaryotes. They are easily differentiated from bifidobacteria on the basis of their guanine and cytosine content, which is under 54% (in bifidobacteria, said content exceeds 54%). The genus comprises nearly 80 species, which are catalase-negative, immobile, sporeless, cytochrome-oxidase-negative, non-gelatin-hydrolysing and non-indole-producing, with a saccharolytic and microaerophilic metabolism. They also have particular nutritional requirements, namely soluble carbohydrates, free amino acids, peptones, fatty acids and their esters, salts, nucleic acids and vitamins. They are also classified on the basis of the type of fermentation as obligate homofermenting, obligate heterofermenting and facultative heterofermenting species.

Lactic acid bacteria of the *rhamnosus* species in particular were originally identified and selected from strains of human intestinal origin. They have different specific characteristics which they only partly share with other lactate-producing bacteria:

1) from the immunological standpoint they improve the T and B lymphocyte response and the "natural killer" (NK) response of the CD56+ cells;

2) from the clinical standpoint their use is an effective method of combating various forms of diarrhea (including rotavirus, travellers' diarrhea, diarrhea caused by antibiotic treatments, and recurrent diarrhea caused by superinfections with *Clostridium difficile*);

3) they are also reported to reduce colonisation of the upper airways by pathogens.

As regards colonisation, they are known to be resistant to gastric acidity, bile and the high pH values typical of the large intestine where, after colonisation, they promote the proliferation of bifidobacteria by favourably influencing the environmental conditions.

The genus *Bifidobacterium* comprises 28 species, and presents the following general characteristics: Gram-positive, anaerobic, immobile, sporeless, catalase-negative, non-acid uric, pleomorphic and acetic-acid-producing (as well as lactate-producing). They also use ammonium salts as a source of nitrogen, and are able to synthesise many vitamins. Finally, their development is influenced by the presence of bifidogenic factors (oligosaccharides and peptones).

As already stated, during their transit and colonisation, lactobacilli and bifidobacteria perform a series of actions, identifiable as physiological, such as reduction of lactose intolerance; improvement of intestinal motility; reduction of serum cholesterol; accumulation of proteolytic enzymes, proteins and vitamins; regulation of nutrient absorption; reactivation of the permeability of the intestinal epithelium; and improvement of the conditions of geriatric patients.

They are also characterised by "non-physiological" effects such as an anti-diarrhea effect (infantile diarrhea, travellers' diarrhea and diarrhea associated with the use of antibiotics); an antiseptic effect (due to the production of bacteriocins, lactic acid and acetic acid and to the release of acetyl, acetic aldehyde, hydrogen peroxide and carbon dioxide); an anti-tumoral effect (mainly located in the colon and rectum); and an immunomodulating effect (patients treated with these strains have better NK cell, antibody, phagocyte and cytokine responses).

Moreover, a series of biological activities performed by these various strains is under discussion, and should soon be confirmed by further studies, such as an anallergic activity (in the food sphere), anti-inflammatory activity (in the intestinal sphere), antioxidant activity (with favourable repercussions on the atherosclerotic sphere), and liver-protecting activity (especially in the sphere associated with alcohol consumption).

According to a preferred aspect of the invention, the mixture of probiotic components comprises *Bifidobacterium longum* and at least one further species selected from the group of bacteria consisting of *Lactobacillus helveticus, Lactobacillus acidophilus, Lactobacillus rhamnosus* and *Lactobacillus plantarum*.

In the aforementioned mixture of probiotic components, it is preferred that that the *Bifidobacterium longum* is *Bifidobacterium longum* R175 ("Rosell 175"), that the *Lactobacillus helveticus* is *Lactobacillus helveticus* R52 ("Rosell 52"); that the *Lactobacillus rhamnosus* is *Lactobacillus rhamnosus* R11 ("Rosell 11"), and that the *Lactobacillus plantarum* is *Lactobacillus plantarum* R1012 ("Rosell 1012"). *Lactobacillus helveticus* Rosell 52 is also known in the industry as a *Lactobacillus acidophilus* species and therefore as used herein, *Lactobacillus helveticus* R52 may also be known as *Lactobacillus acidophilus* R52.

*Bifidobacterium longum* R175 is available from Institut Rosell Inc. (Lallemand), Montreal, Qc, Canada under product code 75119.

*Bifidobacterium longum* R175 is a strict anaerobe, consisting of Gram+ rods of various shapes, isolated or in pairs (1-1.5 µm×6 µm). It forms small white colonies on selective media. *Bifidobacterium longum* R175 is heterofermentative and produces both, I-lactic acid and acetic acid during fermentation. It is catalase negative. In laboratory conditions, *Bifidobacterium longum* R175 grows well in commercially available media for lactic acid bacteria (RCM) at 37° C. under anaerobic conditions. In particular, it is able to grow on the following sugars (API 50 CH results after 48 hours at 37° C.):

| | | | | |
|---|---|---|---|---|
| control − | galactose + | α-methyl-D-mannoside − | melibiose + | D-turanose + |
| Glycerol − | D-glucose + | α-methyl-D-glucoside − | sucrose + | D-lyxose − |
| Erythritol − | D-fructose + | N-acetylglucosamine − | trehalose − | D-tagatose − |
| D-arabinose − | D-mannose + | amygdalin − | inulin − | D-fucose − |
| L-arabinose + | L-sorbose − | arbutin − | melezitose + | L-fucose − |
| Ribose − | rhamnose − | esculin − | D-raffinose + | D-arabitol − |
| D-xylose + | dulcitol − | salicin − | starch − | L-arabitol − |
| L-xylose − | inositol − | cellobiose − | glycogen − | gluconate − |
| Adonitol − | mannitol − | maltose + | xylitol − | 2-ketogluconate − |
| β-methylxyloside − | sorbitol − | lactose + | β-gentobiose − | 5-ketogluconate − |

Moreover, *Bifidobacterium longum* R175 shows the following antibiotic resistance profile:

| Antimicrobial agent | dose | outcome |
|---|---|---|
| Ampicillin | 10 mcg | susceptible |
| Bacitracin | 10 units | susceptible |
| cephalothin | 30 mcg | susceptible |
| chloramphenicol | 30 mcg | susceptible |
| erythromycin | 15 mcg | susceptible |
| gentamycin | 10 mcg | resistant |
| kanamycin | 30 mcg | resistant |
| lincomycin | 2 mcg | intermediate |
| Neomycin | 30 mcg | resistant |
| nitrofurantoin | 300 mcg | susceptible |
| novobiocin | 30 mcg | susceptible |
| penicillin G | 10 units | susceptible |
| Polymyxin B | 300 units | resistant |
| Rifampin | 5 mcg | susceptible |
| streptomycin | 10 mcg | resistant |
| sulfisoxazole | 300 mcg | resistant |

| Antimicrobial agent | dose | outcome |
| --- | --- | --- |
| tetracycline | 30 mcg | susceptible |
| Vancomycin | 30 mcg | susceptible |

*Lactobacillus helveticus* R52 was registered with CNCM (Institut Pasteur) as number I-1722.

*Lactobacillus rhamnosus* R11 was registered with CNMC (Institut Pasteur) as number I-1720 and further under number 990411 at the Canadian Food Inspection Agency.

*Lactobacillus plantarum* R1012 was registered with CNMC (Institut Pasteur) as number MA 18/5U.

A particularly preferred mixture of probiotic components comprises *Bifidobacterium longum*, preferably *Bifidobacterium longum* R175 in combination with *Lactobacillus*, preferably *Lactobacilths helveticus* R52 in combination with, and/or *Lactobacillus plantarum*, preferably *Lactobacillus plantarum* R1012.

The above-identified specific mixture of probiotics present characteristics of stability, adherence, colonising and proliferation capacity ideal for the purposes of the invention.

According to a preferred aspect thereof, the compositions according to the invention will contain the species of bacteria which constitute the mixture of probiotics in the following amounts:

*Bifidobacterium longum* 50 billion CFU/g;
*Lactobacillus helveticus* 150 billion CFU/g;
*Lactobacillus plantarum* 150 billion CFU/g Yet another aspect of the invention, the preferred mixture of probiotic components comprises *Bifidobacterium longum* and *Lactobacillus rhamnosus*.

The above-identified specific mixtures of probiotics present characteristics of stability, adherence, colonising and proliferation capacity ideal for the purposes of the invention.

In a preferred aspect of the invention, the compositions of the present invention will contain the species of bacteria which constitute the mixture of probiotics in the following amounts:

*Bifidobacterium longum* 50 billion CFU/g
*Lactobacillus rhamnosus* 150 billion CFU/g.

In a preferred embodiment, the mixture of probiotic components comprises *Bifidobacterium longum*, preferably *Bifidobacterium longum* R175 and *Lactobacillus rhamnosus*, preferably *Lactobacillus rhamnosus* R11.

In order to enhance and/or improve the survival of the probiotic species it is preferred that the probiotic species are combined with a carrier comprising non-probiotic ingredients that not only serve as a food source for the probiotics but also help to enhance the overall effectiveness of the composition as a whole.

It has been demonstrated that when lactobacilli and bifidobacteria are administered to modulate the intestinal flora, the effect can be transient, because the proliferation of exogenous bacteria can be limited. The inventors have shown that *Bifidobacterium*, specifically *Bifidobacterium longum* has poor survival when administered along. Supplementation combined with prebiotics is required to solve this problem. The inventors have surprisingly found that when a probiotic component, more specifically *Bifidobacterium longum*, is administered with a carrier comprising a prebiotic, the survival of the *Bifidobacterium longum* is improved and/or enhanced.

Prebiotics are substances used to provide suitable selective nutrition to specific bacterial groups, called the probiotic fraction, in order to support their resistance, colonising capacity and reproductive capacity in the intestine. In chemical terms, prebiotic substances correspond to digestible and indigestible carbohydrates and dietary fibers. After being ingested, these substances pass through nearly all of the upper gastrointestinal tract intact, without undergoing any digestive process. When they reach the colon, they represent the main nutrient substrate of the healthy/commensal bacteria whose presence is to be supported, which can use these substances and digest them so they serve as a nutrient substrate.

Not all the substances grouped under the term "prebiotic" have the same specific features.

Prebiotics are a family of food ingredients which are very different from one another, and which stimulate and facilitate the growth of some bacterial species in a different way from compound to compound.

The most widely studied prebiotics are inulin and fructooligosaccharides (FOS).

Inulin, described for the first time in the early 19th century, is found in many plants. Inulin extracted from chicory is currently preferred for dietary use. The addition of inulin to a product (which makes it a "symbiotic") guarantees the presence of the nutritional substrate essential to the physiological balance of the entire microbial flora. When inulin, a non-hydrolysable polysaccharide, breaks down (which can only result from bacterial action), it reduces the intestinal pH, thus keeping the environmental of the colon uninhabitable for pathogen growth.

FOS are also widely used prebiotics. In chemical terms they are short-chain fructans, and consequently soluble, with a degree of polymerisation not exceeding 8 carbohydrate units. From the biological standpoint, the addition of this mixture of prebiotics appears to be suitable and successful: as recently reported, these prebiotics considerably modify the composition of the intestinal microflora, for example increasing the bifidobacteria from 20 to 71% of the entire intestinal population.

The carrier for use in the probiotic compositions of the present invention preferably comprise a prebiotic, such as a fiber component. The prebiotic can serve as a food source for probiotic species such as *Lactobacillus* and *Bifidobacteria*. In the upper gastrointenstinal tract the *Bifidobacterium* do not growth because of the oxygen environment, but the *Lactobacillus* can be metabolically active. If an organism's enzymatic processes become active, they will seek a source of food. The synergistic relationship between the *Lactobacillus* as probiotics and a prebiotic, preferably inulin can cause the lactobacilli to undergo metabolic activity. This can be beneficial to the host as noted before, but would also mean that the cells may not survive the physiological action within the gastrointestinal tract. Thus, the positive synergistic relationship between the Lactobacilli and the inulin in the upper GI tract can be thought to enhance the immune-potentiating ability of the probiotic containing compositions of the present invention, over that of the individual *lactobacillus* strains that do not have the prebiotic present, but this synergistic relationship would be at the expense of percent cumulative survival.

The carrier compositions of the compositions of the present invention further act to combat the microenvironment, typical of intestinal disorders, which counteracts effective colonisation following supplementation with probiotics. Probiotics often find an environment characterised by inflammation, alteration of tissue osmosis, and prooxidative situations, associated with the presence of free cations, which prevent probiotic colonisation. However, the composition thus developed allows very high rates of gastroenteric colonisation because it prepares the substrate for effective colonisation simultaneously with the arrival of the probiotic mixture.

As regards the prebiotic components, in this respect carbohydrates and fibers like GOS, xylooligosaccharides, indigestible maltodextrins, inulin, isomaltooligosaccharides, lactitol, lactulose and transgalactooligosaccharides may be employed, even though inulin, fructose and/or fructooligosaccharides (FOS) are particularly preferred in the context of the present invention. In a most preferred embodiment the prebiotic component comprises inulin, fructose and/or FOS.

In a preferred embodiment the probiotic containing compositions of the present invention comprise one or more prebiotics in an amount up to about 80% of the total composition. In a more preferred embodiment, the prebiotic is a combination of inulin and fructose. The inulin is present in an amount of about 0 to about 100% of the carrier composition; more preferably inulin is present in an amount of about 10 to about 100% of the carrier; most preferably the inulin is about 20% of the carrier. The fructose is present in an amount of about 1 to about 100% of the carrier composition; more preferably fructose is present in an amount of about 1 to about 100% of the carrier composition; most preferably the fructose is present in an amount greater than 50% of the carrier of the composition.

The carrier composition further comprises lactoferrin. Lactoferrin is a particular glycoprotein with a weight of 80,000 daltons, which has been described since 1939. It binds the free iron normally found in breast milk, saliva, tears, the secondary secretory granules of the neutrophils, and the mucous secretions.

Lactoferrin has various activities, especially antibacterial and anti-inflammatory activity. As demonstrated by numerous studies, lactoferrin exhibits a particular affinity for bonding with the outer wall of Gram-negative bacteria and with free iron: by means of the first action mechanism, lactoferrin exerts its "killing" capacity on pathogenic bacteria, and by means of the second it chelates free iron and removes it from the microenvironment.

Lactoferrin, as well as limiting the intestinal growth of pathogenic bacteria, exerts anti-inflammatory and free-radical scavenging properties. This dual capacity is particularly important in the intestine, where pathogenic bacteria sometimes find the ideal conditions for proliferating dangerously, as the typical pH of this organ limits the correct operation of transferrin, a protein normally responsible for removing free iron, which is a source of free radicals and consequent damage to the intestinal mucous membranes. In a preferred embodiment the carrier composition comprises lactoferrin in an amount of about 0 to about 10%; more preferably the lactoferrin is present in an amount of about 0.1% to about 5%; most preferably the lactoferrin is present in an amount of about 0.5%.

Lactoferrin has also been described to function as a prebiotic, providing a substrate for fermentation by commensal bacteria.

The mineral salts employed in the embodiments of the present invention are one or more selected from the group consisting of magnesium, potassium, zinc, and optionally copper and the salts thereof, including but not limited to magnesium gluconate, potassium citrate, zinc gluconate and copper citrate.

As is well-known, during illnesses, cell and tissue metabolism leads, especially if associated with a loss of liquids, to a loss of sodium, potassium, magnesium and chlorine. These electrolytes are essential to the correct functioning of the muscle fibre cells (including the smooth intestinal muscle fibre cells), the electrolyte balance and the osmotic balance of the cells and tissues. In particular, a reduction in the potassium and magnesium reserves generates weakness, inefficient muscle contractions and a pulse transmission deficiency in the neuromuscular plate, cramps. The addition of magnesium and/or potassium prevents deficiencies in the event of stress, infection, increased environmental temperature, physical effort, diarrhea, etc.

Magnesium is present in the carrier composition of the present invention in an amount of about 0 to about 100%; more preferably magnesium is present in an amount of about 5 to about 20%; most preferably about 14 to about 16% of the carrier composition. Most preferably the magnesium is present as magnesium gluconate.

Potassium is present in the carrier composition of the present invention in an amount of about 0 to about 100%; more preferably potassium is present in an amount of about 0.1 to about 10%; most preferably about 5% of the carrier composition. Most preferably the potassium is present as potassium citrate.

Zinc is a vital element which is vital to support the activity of over 100 enzymes, including DNA and RNA polymerases, where it operates as a coenzyme. A mild zinc deficiency leads to a slight hypofunction of the immune system, with a consequently increased risk of cold-related disorders (such as parainfluenza and influenza syndromes). In children, a mild zinc deficiency may lead to a slight delay in growth, while a serious deficiency causes arrested growth and hypogonadism. Finally, the absence of zinc during pregnancy is teratogenic. The presence of zinc promotes the functioning of the immune system. Zinc is present in the carrier composition of the present invention in an amount of about 0 to about 100%; more preferably zinc is present in an amount of about 0.1 to about 20%; most preferably about 5% of the carrier composition. Most preferably the zinc is present as zinc gluconate.

Optionally, copper can be added to the carrier of the present invention. Copper is an element which is absorbed at intestinal level via specific transport mechanisms. In the liver, it is conjugated with ceruloplasmin, as a result of which it is distributed in all tissues. It is excreted through the bile and faeces. In the tissues, copper is part of the structure of numerous enzymes including amino-oxidase, iron-oxidase, superoxide dismutase, tyrosinase, etc. Copper deficiency, which is uncommon, can cause leucopenia, anaemia, musculoskeletal dysfunctions, and skin depigmentation. A deficiency during pregnancy can lead to a lower birth weight of the baby. Copper, if present, normalises the immune functions, above all helping to combat winter illnesses supported by common viruses.

Optionally, the carrier composition of the present invention may further comprise glutathione and/or arabinogalactans.

Glutathione, also known as GSH, is a tripeptide consisting of glycine, cystine and glutamate. It operates inside the cells as a cofactor of the enzymes glutathione-transferase and glutathione-peroxidase, which are used by the cells to demolish lethal molecules such as hydrogen peroxide. Due to the presence of a sulphydryl group, glutathione can pass alternately from the reduced form to the oxidised form, acting as an antioxidant. Due to its ability to react with oxidising substances such as free radicals, hydroperoxides and lipoperoxides, it is therefore essential, and is considered a key enzyme in preventing cell aging. Although it is a peptide, gastroprotection is unnecessary because it is poorly hydrolysed by the gastric juices and the peptidases present. Oral absorption is very good, and takes place in the intestine. It was also administered recently at high doses to patients undergoing oncological and HIV treatment. The product is very safe. No toxicity data seem to exist. Patients' compliance and the tolerability of the product are also very high. Glutathione, if present, strengthens the body antioxidant defences and prevents cell and tissue aging. Glutathione is present in the carrier composition of the present invention in an amount of about 0 to about 20%; more preferably glutathione is present in an amount of about 0.1 to about 5%; most preferably about 1% of the carrier composition.

Arabinogalactans are polysaccharides with a high molecular weight (around 200,000 daltons), whose main chain is a polymer of galacturonic acid which is partly carboxymethylated and acetylated in lateral positions with rhamnogalacturonans. From the biological standpoint they are strong macrophagic stimulators (in human and murine macrophages an excellent increase in nitric oxide production is observed during phagocytic activity if it is stimulated by these compounds) and stimulate the activity of the T cells (in both helper and cytotoxic populations).

Arabinogalactans, if present, perform an immunostimulating action and boost the response to infection by pathogens. More in particular, the optional addition of a potent unabsorbed T-specific immunogen (arabinogalactan) may allow activation of the local T-specific response, which takes place in the lymph node areas of the intestine (Peyer's patches), thus causing a reduction in the pathogenic fraction simultaneously with the arrival of the pyogenic probiotic fraction. The simultaneity of the two events further facilitates the events of colonisation and proliferation, which are otherwise rendered difficult by the T-sensitive pathogenic fraction.

Optionally, the compositions of the present invention further comprise saccharomycetes or yeasts. The presence of saccharomycetes or yeasts (if used) is justified by the fact that they release trace elements and vitamins with nutritional value and compete with pathogens. Yeasts may also be employed in the form of a lysate enriched with glucans, i.e. polysaccharide structures which limit bacterial adherence of pathogens to the intestinal mucosa. According to a preferred embodiment, the compositions according to the invention may contain in particular *Saccharomyces cerevisae* and/or *boulardii*. According to a particularly preferred embodiment, the *Saccharomyces boulardii* employed by the present invention is *Saccharomyces boulardii* ATCC 74012.

As regards the further optional addition of ingredients which are not directly probiotic, their main aim is likewise to provide an additional prebiotic advantage; the foregoing applies e.g. to cysteine transporters, such as N-acetylcysteine and the like; the same applies to ingredients with a chelating action on free cations and anions like procyanidins, anthocyans and catechins with any degree of polymerisation, and the like; and the same applies to elements which already modulate the immune response at enteric level, like the various species of *Echinacea, Uncaria* and *Astragalus*. Finally, the same applies to the addition of macro- or micronutrients and water- or fat-soluble vitamins. Lastly, the addition of antioxidants may further have a protective effect upon the probiotics contained in the compositions of the present invention.

It has been found that the compositions according to the invention possess a considerable health-improving activity, maintain and/or restore intestinal health, prevent the consequences of stress and perform an anti-inflammatory and immunomodulating action. At the same time, they guarantee effective colonisation. The effect of the compositions according to the invention is greater than that obtained following separate administration of the individual components of the combination, apparently due to synergy between the various components.

Particularly preferred compositions of the present invention contain:

a) a mixture of probiotic components comprising *Bifidobacterium longum* R175, *Lactobacillus helveticus* R52, and *Lactobacillus plantarum* R1012;

b) a carrier comprising:
1) prebiotic component comprising inulin and fructose:
2) lactoferrin;
3) a mixture of mineral salts consisting of magnesium, potassium, and zinc salts; and
4) glutathione.

In a most preferred embodiment, the compositions of the present invention contain:

a) a mixture of probiotic components comprising *Bifidobacterium longum* 50 billion CFU/g; *Lactobacillus helveticus* 150 billion CFU/g; and *Lactobacillus plantarum* 150 billion CFU/g; and b) a carrier comprising:
1) a mixture of prebiotics comprising about 80% of the total carrier composition wherein the prebiotics are inulin and fructose, wherein the inulin is present in an amount of about 10 to about 100% of the carrier composition; most preferably the inulin is about 20% of the carrier and fructose is present in an amount of about 1 to about 100% of the carrier composition; more preferably fructose is present in an amount of about 1 to about 100% of the carrier composition; most preferably the fructose is present in an amount greater than 50% of the carrier of the composition;

2) lactoferrin in an amount of about 0 to about 10%; more preferably the lactoferrin is present in an amount of about 0.1% to about 5%; most preferably the lactoferrin is present in an amount of about 0.5%;

3) mineral salts selected from the group consisting of magnesium, potassium and zinc salts, wherein magnesium is present in the carrier composition of the present invention in an amount of about 0 to about 100%; more preferably in an amount of about 5 to about 20%; most preferably about 14 to about 16% of the carrier composition and the magnesium is magnesium gluconate; wherein the potassium is present in an amount of about 0 to about 100%; more preferably potassium is present in an amount of about 0.1 to about 10%; most preferably about 5% of the carrier composition and further the potassium is potassium citrate; and further wherein the zinc is present is present in the carrier composition of the present invention in an amount of about 0 to about 100%; more preferably zinc is present in an amount of about 0.1 to about 20%; most preferably about 5% of the carrier composition and wherein the zinc is present as zinc gluconate; and 4) glutathione, wherein the glutathione is present in the carrier composition of the present invention in an amount of about 0 to about 20%; more preferably glutathione is present in an amount of about 0.1 to about 5%; most preferably about 1% of the carrier composition.

Further particularly preferred compositions of the present invention contain:
a) a mixture of probiotic components comprising *Bifidobacterium longum* R175 and *Lactobacillus rhamnosus* R11; and *Saccharomyces boulardii;* and
b) a carrier comprising:
1) a prebiotic component consisting of inulin and fructose;
2) lactoferrin;
3) a mixture of mineral salts consisting of magnesium, potassium salts and zinc salts; and
4) glutathione.

According to a preferred aspect of the present invention, the herein described compositions will be used to prepare diet supplements.

The compositions according to the invention could be formulated suitably for oral administration, and will be prepared according to conventional methods well known in pharmaceutical technology, such as those described in Remington's Pharmaceutical Handbook, Mack Publishing Co., N.Y., USA, using excipients, diluents, fillers and anti-caking agents acceptable for their final use. Exemplary additional ingredients include citric acid, magnesium oxide, silicon dioxide and other ingredients one skilled in the art would appreciate.

The compositions according to the invention could be formulated, for example, in the form of soluble sachets, orally soluble forms, capsules, tablets chewable tablets, multi-layer tablets with time- and pH-dependent release, and granulates.

The compositions of the present invention can be used to enhance and/or improve the viability and survivability of the probiotic species, more particularly to enhance and/or improve the viability of *Bifidobacterium longum*. Said methods comprise mixing the probiotic component that comprises *Bifidobacterium longum* alone or in combination with one or more probiotic species and a carrier comprising a therapeutically effective amount of one or more prebiotics; a therapeutically effective amount of one or more mineral salts; a therapeutically effective amount of lactoferrin and optionally, a therapeutically effective amount of glutathione. As used herein, "amount" refers to quantity or to concentration as appropriate to the context. The amount of a material that constitutes a therapeutically effective amount varies according to factors such as the potency, efficacy, and the like, of the particular material, the route of administration, and on the dosage form used. A therapeutically effective amount of a particular material can be selected by those of ordinary skill in the art with due consideration of such factors. The concentration of the material depends on the desired dosage.

The such formulated compositions, as herein described, are stable upon storage at room temperature.

Additionally, the compositions of the present invention can also be used to improve and/or enhance the therapeutic effect of the probiotic materials. Since the compositions of the invention have exhibit improved probiotic survival, the formulations are believed to have greater efficacy since a greater amount of the probiotic survives transit through both the upper and lower gastrointestinal tract. Accordingly, the compositions of the present invention can be used to improve and/or enhance the gastrointestinal health and/or immunity in a human subject in need thereof.

Some examples of formulations according to the invention are set out below. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result.

The following Examples are offered to illustrate the claimed method and its practice.

EXAMPLES

Example 1

| NAME OF COMPONENT | | mg/sachet |
|---|---|---|
| Probiotic Material: | | |
| *Lactobacillus helveticus* Rosell 52 | 150 billion CFU/g | 73.333 |
| *Bifidobacterium longum* R175 | 50 billion CFU/g | 20.000 |
| *Lactobacillus plantarum* Rosell 1012 | 150 billion CFU/g | 20.000 |
| Carrier material: | | |
| Magnesium oxide | | 41.446 |
| Magnesium gluconate | | 341.297 |
| Potassium citrate | | 138.290 |
| Zinc gluconate | | 111.111 |
| Glutathione | | 20.000 |
| Lactoferrin | | 11.364 |
| Copper citrate | | 2.834 |
| Inulin | | 500.000 |
| Fructose | | 1291.125 |
| Additional (optional) excipients | | |
| Sucralose | | 4.000 |
| Acesulfame K | | 12.000 |
| Flavouring | | 150.000 |
| Aerosil 200 | | 40.000 |
| Colouring: E124 | | 2.200 |
| Colouring: E102 | | 1.000 |
| Anhydrous citric acid | | 220.000 |

The formulation described above is prepared as follows: *Lactobacillus Plantarum, Lactobacillus helveticus, Bifidobacterium longum*, are mixed with inulin and blended at 32 rpm for approximately 10 min. Thereafter, fructose, magnesium gluconate, zinc gluconate, citric acid, flavor, potassium citrate, magnesium oxide, silicon dioxide, glutathione, potassium acesulfame, lactoferrine, and sucralose are added to the mixture and blended at 32 rpm for another 10 min.

Example 2

| NAME OF COMPONENT | | mg/sachet |
|---|---|---|
| Probiotic materials: | | |
| *Saccharomyces boulardii* | 20 billion CFU/g | 100.000 |
| *Bifidobacterium longum* R175 | 50 billion CFU/g | 20.000 |
| *Lactobacillus rhamnosus* Rosell 11 | 150 billion CFU/g | 46.667 |
| Carrier materials: | | |
| Magnesium gluconate | | 511.945 |
| Zinc gluconate | | 50.000 |
| Lactoferrin | | 11.364 |
| Fructose | | 2585.024 |
| Inulin | | 500.000 |
| Additional (optional) excipients | | |
| Apricot flavouring 502168AP0551 | | 70.000 |
| Anhydrous citric acid | | 50.000 |
| Colouring: 1% betacarotene | | 28.000 |

-continued

| NAME OF COMPONENT | mg/sachet |
|---|---|
| Sucralose | 7.000 |
| Aerosil 200 | 20.000 |
| TOTAL | 4000.00 |

Example 3

| NAME OF COMPONENT | | mg/sachet |
|---|---|---|
| Probiotic materials: | | |
| *Lactobacillus helveticus* Rosell 52 | 150 billion CFU/g | 73.333 |
| *Bifidobacterium longum* R175 | 50 billion CFU/g | 20.000 |
| *Lactobacillus plantarum* Rosell 1012 | 150 billion CFU/g | 20.000 |
| Carrier: | | |
| Magnesium oxide | | 41.446 |
| Magnesium gluconate | | 341.297 |
| Potassium citrate | | 138.290 |
| Zinc gluconate | | 111.111 |
| Glutathione | | 20.000 |
| Lactoferrin | | 11.364 |
| Inulin | | 500.000 |
| Fructose | | 1335.678 |
| Additional (optional) excipients: | | |
| Sucralose | | 4.000 |
| Acesulfame K | | 12.000 |
| Flavouring | | 150.000 |
| Aerosil 200 | | 40.000 |
| Colouring: E124 | | 2.200 |
| Colouring: E102 | | 1.000 |
| Anhydrous citric acid | | 220.000 |
| TOTAL | | 3000.00 |

The formulation described above is prepared as follows: *Lactobacillus plantarum, Lactobacillus helveticus, Bifidobacterium longum*, are mixed with inulin and blended at 32 rpm for approximately 10 min. Thereafter, fructose, magnesium gluconate, zinc gluconate, citric acid, flavor, potassium citrate, magnesium oxide, silicon dioxide, glutathione, potassium acesulfame, lactoferrine, and sucralose are added to the mixture and blended at 32 rpm for another 10 min.

Example 4

The probiotic species contained in the formulation described in Example 3 were tested to determine the survival rate of the probiotics. Survival of the probiotic strains in the composition of the present invention as compared to the individual strains, were tested in a dynamic, in vitro model of the upper gastrointestinal tract, also known as TIM-1. The TIM-1 model can simulate conditions in the gastric chamber and small intestine of the human, and thus can be used to evaluate percent cumulative survival of probiotics as they transit the upper gastrointestinal tract.

The composition of Example 3 tested in TIM-1 contained a total amount of probiotic cells (colony forming units, or CFU) of $9.81 \times 10E9$ CFU on enumeration. When the individual levels of the probiotic strains contained in the composition of Example 3 were assessed, the amount of each strain quantified by microbial plating was:
*Lactobacillus helveticus* $8.0 \times 10E9$ CFU
*Lactobacillus plantarum* $8.7 \times 10E8$ CFU
*Bifidobacterium longum* $9.1 \times 10$ E8 CFU The level quantified for each probiotic strain in the composition of Exhibit 3 was the target level used when testing the individual strains in the TIM-1 model. In other words, the level of the probiotic strains, whether in the product or individually, was set to be $8 \times 10E9$ CFU for *L. helveticus*, $8.7 \times 10E8$ CFU for *L. plantarum* and $9.1 \times 10E8$ CFU for *B. longum*.

In the actual experiments, the individual probiotic strains and the composition of Exhibit 3 are administered with a meal (light European continental breakfast). So, the final amount of each strain, when mixed with the meal, was confirmed and thus, the average starting level for each probiotic that was used, both individually as well as in the composition of Exhibit 3, was:
*Lactobacillus helveticus* $8.6 \times 10E9$ CFU;
*Lactobacillus plantarum* $7.0 \times 10E8$ CFU;
*Bifidobacterium longum* $1.4 \times 10E9$ CFU.

The results of the TIM-1 test are outlined in the Table below:

| Probiotic Strain | | % cumulative survival | Avg % cumulative survival | Colony Forming Units (CFU) |
|---|---|---|---|---|
| *Lactobacillus* | Run 1a | 2.20 | 1.4 | $1.2 \times 10E8$ CFU |
| *helveticus* | Run 2a | 0.44 | | |
| | Run 1b | 2.55 | | |
| | Run 2b | 0.49 | | |
| *Lactobacillus* | Run 1a | 12.45 | 9.7 | $6.8 \times 10E7$ CFU |
| *plantarum* | Run 2a | 5.63 | | |
| | Run 1b | 12.92 | | |
| | Run 2b | 7.77 | | |
| *Bifidobacterium* | Run 1a | 29.55 | 42.9 | $6.0 \times 10E8$ CFU |
| *longum* | Run 2a | 31.20 | | |
| | Run 1b | 68.55 | | |
| | Run 2b | 42.11 | | |

Thereafter, each of the strains identified below were individually tested through the TIM-1. The data is presented below in the table below.

| Probiotic Strain | | % cumulative survival | Avg % cumulative survival | Colony Forming Units (CFU) |
|---|---|---|---|---|
| *Lactobacillus* | Run 1 | 13.11 | 13.1 | $1.1 \times 10E9$ CFU |
| *helveticus* | Run 2 | 13.15 | | |
| *Lactobacillus* | Run 1 | 45.17 | 39.2 | $2.7 \times 10E8$ CFU |
| *plantarum* | Run 2 | 33.24 | | |
| *Bifidobacterium* | Run 1 | 0.01 | 0.02 | $2.8 \times 10E5$ CFU |
| *longum* | Run 2 | 0.02 | | |

These data show that there is a synergistic effect of the composition. More specifically, the number of *Bifidobacterium longum* probiotic cells that survive transit thru the upper gastrointestinal tract is more than 1000-fold more (greater than $3_{log\ 10}$) than when tested without the other probiotics and carrier. The *Bifidobacterium longum* when administered independent of the composition of the invention did not demonstrate robust survival. In fact the *Bifidobacterium longum* had only a 0.02% cumulative survival when administered by itself compared to 42.9% cumulative survival when administered in combination with *Lactobacillus helveticus, Lactobacillus plantarum* and the carrier comprising: a prebiotic (inulin and fructose), zinc gluconate, magnesium gluconate, potassium citrate; glutathione and lactoferrin; and optionally citric acid, magnesium oxide and silicon dioxide.

Example 5

The probiotic species contained in the formulation described in Example 3 were tested to determine the survival rate of the probiotics. Survival of the probiotic strains in the composition of the present invention as compared to the individual strains, were tested in a dynamic, in vitro model of the lower gastrointestinal tract, also known as TIM-2. The TIM-2 in vitro gastrointestinal model simulates to a high degree the dynamic processes in the (proximal part of the) large intestine, and this system has been validated successfully with regards to the number and ratio of the various micro-organisms which are similar in composition and metabolic activity with that of the human colon.

The individual probiotic strains in the formulation of Example 3 and the formulation of Example 3 were tested separately in TIM-2. All runs in TIM-2 were carried out in duplicate. In each run, the formulation to be tested was introduced into a TIM-2 system which was inoculated with a standardized dense microbiota prepared from fecal material of healthy human adults. The formulation was added to the system once a day. A standardized meal (SIEM; Standard Ileal Efflux Medium, containing amongst others (g/day): 0.6 pectin, 0.6 xylan, 0.6 arabinogalactan, 0.6 amylopectin, 3.0 casein, 5.0 starch, 2.16 Tween 80, 3.0 bactopepton, 0.05 bile) was continuously fed to TIM-2. As a control, a standard TIM-2 run (with only SIEM added) was performed in duplicate. The effect of the formulation on the metabolic activity and composition of the microbiota was determined and compared to the control.

During the fermentation runs in the TIM-2 system, 24 h sampling was done. The lumen and dialysis samples were analysed gas-chromatographically on the concentrations of SCFA and BCFA. Additional samples were analyzed enzymatically for lactate and ammonia. The concentrations of these metabolites found in the lumen and dialysis samples were collectively used to calculate the cumulative production of the metabolites in time.

Short-chain fatty acids and lactate are considered beneficial microbial metabolites. L-lactate is considered more beneficial than D-lactate. Lactate only accumulates when there is a fast fermentation. If substrates are fermented slowly, lactate is converted into other metabolites, such as short-chain fatty acids, and does not accumulate.

The results of the TIM-2 study are summarized in the tables below.

| Cumulative SCFA production (mmol) in time of all TIM-2 variables | | | | | | | | | | | | | | | | |
|---|---|---|---|---|---|---|---|---|---|---|---|---|---|---|---|---|
| | #14-03, run 1 | | | | #14-03, run 2 | | | | average | | | | range | | | |
| #14-03 time (h) | acetate | propionate | n-butyrate | total | acetate | propionate | n-butyrate | total | acetate | propionate | n-butyrate | total | acetate | propionate | n-butyrate | total |
| 0 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| 24 | 19.21 | 5.06 | 9.25 | 33.52 | 17.20 | 2.80 | 5.91 | 25.91 | 18.20 | 3.93 | 7.58 | 29.72 | 1.00 | 1.13 | 1.67 | 3.80 |
| 48 | 49.32 | 32.26 | 16.32 | 97.90 | 45.23 | 14.61 | 12.97 | 72.80 | 47.27 | 23.43 | 14.65 | 85.35 | 2.05 | 8.83 | 1.68 | 12.55 |
| 72 | 79.71 | 61.72 | 25.90 | 167.33 | 84.18 | 45.46 | 19.36 | 149.00 | 81.94 | 53.59 | 22.63 | 158.16 | 2.24 | 8.13 | 3.27 | 9.17 |

| | #15-03, run 1 | | | | #15-03, run 2 | | | | average | | | | range | | | |
|---|---|---|---|---|---|---|---|---|---|---|---|---|---|---|---|---|
| #15-03 time (h) | acetate | propionate | n-butyrate | total | acetate | propionate | n-butyrate | total | acetate | propionate | n-butyrate | total | acetate | propionate | n-butyrate | total |
| 0 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| 24 | 21.86 | 11.44 | 11.04 | 44.34 | 31.65 | 10.13 | 11.17 | 52.95 | 26.75 | 10.78 | 11.10 | 48.64 | 4.90 | 0.65 | 0.06 | 4.30 |
| 48 | 49.01 | 35.14 | 20.26 | 104.41 | 53.22 | 25.18 | 25.13 | 103.54 | 51.12 | 30.16 | 22.70 | 103.98 | 2.11 | 4.98 | 2.44 | 0.44 |
| 72 | 67.53 | 52.74 | 29.94 | 150.20 | 72.43 | 36.35 | 44.41 | 153.19 | 69.98 | 44.54 | 37.17 | 151.70 | 2.45 | 8.19 | 7.24 | 1.49 |

| | #16-03, run 1 | | | | #16-03, run 2 | | | | average | | | | range | | | |
|---|---|---|---|---|---|---|---|---|---|---|---|---|---|---|---|---|
| #16-03 time (h) | acetate | propionate | n-butyrate | total | acetate | propionate | n-butyrate | total | acetate | propionate | n-butyrate | total | acetate | propionate | n-butyrate | total |
| 0 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| 24 | 24.33 | 11.47 | 8.34 | 44.14 | 12.33 | 5.36 | 6.99 | 24.68 | 18.33 | 8.42 | 7.67 | 34.41 | 6.00 | 3.05 | 0.68 | 9.73 |
| 48 | 49.13 | 36.05 | 17.04 | 102.22 | 44.50 | 33.21 | 17.60 | 95.31 | 46.82 | 34.63 | 17.32 | 98.77 | 2.32 | 1.42 | 0.28 | 3.45 |
| 72 | 75.10 | 58.48 | 29.83 | 163.41 | 63.08 | 55.35 | 29.93 | 148.36 | 69.09 | 56.92 | 29:88 | 155.88 | 6.01 | 1.56 | 0.05 | 7.52 |

| | #17-03, run 1 | | | | #17-03, run 2 | | | | average | | | | range | | | |
|---|---|---|---|---|---|---|---|---|---|---|---|---|---|---|---|---|
| #17-03 time (h) | acetate | propionate | n-butyrate | total | acetate | propionate | n-butyrate | total | acetate | propionate | n-butyrate | total | acetate | propionate | n-butyrate | total |
| 0 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| 24 | 28.71 | 7.81 | 10.66 | 47.18 | 22.04 | 10.17 | 8.93 | 41.15 | 25.38 | 8.99 | 9.80 | 44.16 | 3.33 | 1.18 | 0.87 | 3.02 |
| 48 | 59.55 | 24.69 | 22.24 | 106.47 | 44.98 | 34.33 | 18.07 | 97.38 | 52.26 | 29.51 | 20.15 | 101.93 | 7.28 | 4.82 | 2.08 | 4.55 |
| 72 | 87.63 | 38.71 | 37.15 | 163.50 | 63.23 | 53.22 | 33.15 | 149.60 | 75.43 | 45.97 | 35.15 | 156.55 | 12.20 | 7.26 | 2.00 | 6.95 |

| | #18-03, run 1 | | | | #18-03, run 2 | | | | average | | | | range | | | |
|---|---|---|---|---|---|---|---|---|---|---|---|---|---|---|---|---|
| #18-03 time (h) | acetate | propionate | n-butyrate | total | acetate | propionate | n-butyrate | total | acetate | propionate | n-butyrate | total | acetate | propionate | n-butyrate | total |
| 0 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| 24 | 21.48 | 11.71 | 6.67 | 39.86 | 19.46 | 10.54 | 8.07 | 38.07 | 20.47 | 11.12 | 7.37 | 38.97 | 1.01 | 0.59 | 0.70 | 0.89 |
| 48 | 46.86 | 39.89 | 13.70 | 100.45 | 47.04 | 39.99 | 15.84 | 102.86 | 46.95 | 39.94 | 14.77 | 101.66 | 0.09 | 0.05 | 1.07 | 1.21 |
| 72 | 71.01 | 65.82 | 25.89 | 162.72 | 68.70 | 61.95 | 27.23 | 157.88 | 69.85 | 63.89 | 26.56 | 160.30 | 1.15 | 1.94 | 0.67 | 2.42 |

14-03 = Example 3 formula; #15-03 = *L. helveticus* R-52; #16-03 = *L. plantarum* R-1012; #17-03 = *B. longum* R-175; #18-03 = Control

| Cumulative lactate production (mmol) in time of all TIM-2 variables | | | | | | | | | | | |
|---|---|---|---|---|---|---|---|---|---|---|---|
| #14-03 | #14-03, run 1 | | | #14-03, run 2 | | | average | | | range | | |
| time (h) | L | D | total | L | D | total | L | D | total | L | 0 | total |
| 0 | 0.00 | 0.00 | 0.00 | 0.00 | 0.00 | 0.00 | 0.00 | 0.00 | 0.00 | 0.00 | 0.00 | 0.00 |
| 24 | 13.85 | 6.76 | 20.60 | 18.69 | 10.63 | 29.32 | 16.27 | 8.69 | 24.96 | 2.42 | 1.93 | 4.36 |
| 48 | 22.32 | 10.41 | 32.73 | 35.33 | 18.47 | 53.80 | 28.82 | 14.44 | 43.26 | 6.51 | 4.03 | 10.54 |
| 72 | 27.35 | 12.57 | 39.92 | 41.42 | 20.69 | 62.11 | 34.38 | 16.63 | 51.01 | 7.04 | 4.06 | 11.10 |
| #15-03 | #15-03, run 1 | | | #15-03, run 2 | | | average | | | range | | |
| time (h) | L | D | total | L | D | total | L | D | total | L | D | total |
| 0 | 0.00 | 0.00 | 0.00 | 0.00 | 0.00 | 0.00 | 0.00 | 0.00 | 0.00 | 0.00 | 0.00 | 0.00 |
| 24 | −0.74 | 0.84 | 0.10 | 0.00 | 0.40 | 0.40 | −0.37 | 0.62 | 0.25 | 0.37 | 0.22 | 0.15 |
| 48 | 0.56 | 2.08 | 2.64 | 0.86 | 1.17 | 2.04 | 0.71 | 1.63 | 2.34 | 0.15 | 0.45 | 0.30 |
| 72 | 2.15 | 3.68 | 5.83 | 1.33 | 1.67 | 3.00 | 1.74 | 2.67 | 4.42 | 0.41 | 1.01 | 1.42 |
| #16-03 | #16-03, run 1 | | | #16-03, run 2 | | | average | | | range | | |
| time (h) | L | D | total | L | D | total | L | D | total | L | D | total |
| 0 | 0.00 | 0.00 | 0.00 | 0.00 | 0.00 | 0.00 | 0.00 | 0.00 | 0.00 | 0.00 | 0.00 | 0.00 |
| 24 | 0.17 | 0.34 | 0.51 | 0.79 | 1.67 | 2.46 | 0.48 | 1.00 | 1.48 | 0.31 | 0.67 | 0.97 |
| 48 | 1.99 | 2.02 | 4.01 | 2.32 | 2.82 | 5.14 | 2.16 | 2.42 | 4.58 | 0.17 | 0.40 | 0.56 |
| 72 | 2.74 | 2.72 | 5.46 | 2.76 | 3.21 | 5.97 | 2.75 | 2.97 | 5.72 | 0.01 | 0.25 | 0.25 |
| #17-03 | #17-03, run 1 | | | #17-03, run 2 | | | average | | | range | | |
| time (h) | L | D | total | L | D | total | L | D | total | L | D | total |
| 0 | 0.00 | 0.00 | 0.00 | 0.00 | 0.00 | 0.00 | 0.00 | 0.00 | 0.00 | 0.00 | 0.00 | 0.00 |
| 24 | 0.36 | 0.46 | 0.82 | 1.63 | 2.83 | 4.46 | 1.00 | 1.64 | 2.64 | 0.63 | 1.19 | 1.82 |
| 48 | 2.13 | 1.94 | 4.07 | 2.59 | 3.80 | 6.40 | 2.36 | 2.87 | 5.23 | 0.23 | 0.93 | 1.16 |
| 72 | 2.54 | 2.53 | 5.07 | 2.99 | 4.27 | 7.26 | 2.76 | 3.40 | 6.16 | 0.23 | 0.87 | 1.09 |
| #18-03 | #18-03, run 1 | | | #18-03, run 2 | | | average | | | range | | |
| time (h) | L | D | total | L | D | total | L | D | total | L | D | total |
| 0 | 0.00 | 0.00 | 0.00 | 0.00 | 0.00 | 0.00 | 0.00 | 0.00 | 0.00 | 0.00 | 0.00 | 0.00 |
| 24 | −0.12 | 1.11 | 0.99 | 2.58 | 3.10 | 5.68 | 1.23 | 2.10 | 3.33 | 1.35 | 0.99 | 2.35 |
| 48 | 1.31 | 2.37 | 3.68 | 3.49 | 3.93 | 7.42 | 2.40 | 3.15 | 5.55 | 1.09 | 0.78 | 1.87 |
| 72 | 4.13 | 5.15 | 9.29 | 4.01 | 4.47 | 8.48 | 4.07 | 4.81 | 8.88 | 0.06 | 0.34 | 0.41 |

14-03 = Example 3 formula; #15-03 = *L. helveticus* R-52; #16-03 = *L. plantarum* R-1012; #17-03 = *B. longum* R-175; #18-03 = Control

| Cumulative BCFA production (mmol) in time of all TIM-2 variables | | | | | | | | | | | |
|---|---|---|---|---|---|---|---|---|---|---|---|
| #14-03 | #14-03, run 1 | | | #14-03, run 2 | | | average | | | range | | |
| time (h) | i-butyrate | i-valerate | total | i-butyrate | i-valerate | total | i-butyrate | i-valerate | total | i-butyrate | i-valerate | total |
| 0 | 0.00 | 0.00 | 0.00 | 0.00 | 0.00 | 0.00 | 0.00 | 0.00 | 0.00 | 0.00 | 0.00 | 0.00 |
| 24 | 0.00 | 0.00 | 0.00 | 0.00 | 0.00 | 0.00 | 0.00 | 0.00 | 0.00 | 0.00 | 0.00 | 0.00 |
| 48 | 0.00 | 0.07 | 0.07 | 0.00 | 0.00 | 0.00 | 0.00 | 0.04 | 0.04 | 0.00 | 0.04 | 0.04 |
| 72 | 0.00 | 0.53 | 0.53 | 0.14 | 0.60 | 0.74 | 0.07 | 0.56 | 0.63 | 0.07 | 0.03 | 0.10 |
| #15-03 | #15-03, run 1 | | | #15-03, run 2 | | | average | | | range | | |
| time (h) | i-butyrate | i-valerate | total | i-butyrate | i-valerate | total | i-butyrate | i-valerate | total | i-butyrate | i-valerate | total |
| 0 | 0.00 | 0.00 | 0.00 | 0.00 | 0.00 | 0.00 | 0.00 | 0.00 | 0.00 | 0.00 | 0.00 | 0.00 |
| 24 | 0.00 | 0.14 | 0.14 | 0.00 | 0.11 | 0.11 | 0.00 | 0.12 | 0.12 | 0.00 | 0.01 | 0.01 |
| 48 | 0.00 | 0.69 | 0.69 | 0.13 | 0.97 | 1.11 | 0.07 | 0.83 | 0.90 | 0.07 | 0.14 | 0.21 |
| 72 | 0.00 | 1.38 | 1.38 | 0.73 | 2.39 | 3.13 | 0.37 | 1.89 | 2.25 | 0.37 | 0.51 | 0.87 |
| #16-03 | #16-03, run 1 | | | #16-03, run 2 | | | average | | | range | | |
| time (h) | i-butyrate | i-valerate | total | i-butyrate | i-valerate | total | i-butyrate | i-valerate | total | i-butyrate | i-valerate | total |
| 0 | 0.00 | 0.00 | 0.00 | 0.00 | 0.00 | 0.00 | 0.00 | 0.00 | 0.00 | 0.00 | 0.00 | 0.00 |
| 24 | 0.00 | 0.14 | 0.14 | 0.00 | 0.09 | 0.09 | 0.00 | 0.11 | 0.11 | 0.00 | 0.03 | 0.03 |
| 48 | 0.00 | 0.71 | 0.71 | 0.00 | 0.79 | 0.79 | 0.00 | 0.75 | 0.75 | 0.00 | 0.04 | 0.04 |
| 72 | 0.51 | 1.54 | 2.06 | 0.16 | 1.52 | 1.68 | 0.34 | 1.53 | 1.87 | 0.18 | 0.01 | 0.19 |

-continued

Cumulative BCFA production (mmol) in time of all TIM-2 variables

| #17-03 | #17-03, run 1 | | | #17-03, run 2 | | | average | | | range | | |
|---|---|---|---|---|---|---|---|---|---|---|---|---|
| time (h) | i-butyrate | i-valerate | total | i-butyrate | i-valerate | total | i-butyrate | i-valerate | total | i-butyrate | i-valerate | total |
| 0 | 0.00 | 0.00 | 0.00 | 0.00 | 0.00 | 0.00 | 0.00 | 0.00 | 0.00 | 0.00 | 0.00 | 0.00 |
| 24 | 0.00 | 0.06 | 0.06 | 0.10 | 0.22 | 0.32 | 0.05 | 0.14 | 0.19 | 0.05 | 0.08 | 0.13 |
| 48 | 0.00 | 0.49 | 0.49 | 0.16 | 1.04 | 1.19 | 0.08 | 0.76 | 0.84 | 0.08 | 0.28 | 0.35 |
| 72 | 0.46 | 1.71 | 2.17 | 0.21 | 1.77 | 1.98 | 0.33 | 1.74 | 2.07 | 0.12 | 0.03 | 0.10 |

| #18-03 | #18-03, run 1 | | | #18-03, run 2 | | | average | | | range | | |
|---|---|---|---|---|---|---|---|---|---|---|---|---|
| time (h) | i-butyrate | i-valerate | total | i-butyrate | i-valerate | total | i-butyrate | i-valerate | total | i-butyrate | i-valerate | total |
| 0 | 0.00 | 0.00 | 0.00 | 0.00 | 0.00 | 0.00 | 0.00 | 0.00 | 0.00 | 0.00 | 0.00 | 0.00 |
| 24 | 0.00 | 0.07 | 0.07 | 0.26 | 0.25 | 0.50 | 0.13 | 0.16 | 0.29 | 0.13 | 0.09 | 0.21 |
| 48 | 0.12 | 0.84 | 0.96 | 1.03 | 1.43 | 2.45 | 0.57 | 1.13 | 1.70 | 0.45 | 0.29 | 0.75 |
| 72 | 0.57 | 1.72 | 2.29 | 1.60 | 2.27 | 3.87 | 1.09 | 1.99 | 3.08 | 0.51 | 0.28 | 0.79 |

14-03 = Example 3 formula; #15-03 = *L. helveticus* R-52; #16-03 = *L. plantarum* R-1012; #17-03 = *B. longum* R-175; #18-03 = Control Cumulative ammonia production (mmol) in time of all TIM-2 variables

| #14-03 time (h) | run 1 | run 2 | average | range |
|---|---|---|---|---|
| 0 | 0.00 | 0.00 | 0.00 | 0.00 |
| 24 | 5.16 | 6.65 | 5.91 | 0.74 |
| 48 | 17.43 | 19.75 | 18.59 | 1.16 |
| 72 | 33.83 | 39.82 | 36.82 | 2.99 |

| #15-03 *L. helveticus* R-52 | | | | |
|---|---|---|---|---|
| time (h) | run 1 | run 2 | average | range |
| 0 | 0.00 | 0.00 | 0.00 | 0.00 |
| 24 | 14.44 | 13.46 | 13.95 | 0.49 |
| 48 | 31.76 | 32.18 | 31.97 | 0.21 |
| 72 | 52.79 | 57.40 | 55.09 | 2.31 |

| #16-03 *L. plantarum* R-1012 | | | | |
|---|---|---|---|---|
| time (h) | run 1 | run 2 | average | range |
| 0 | 0.00 | 0.00 | 0.00 | 0.00 |
| 24 | 12.68 | 14.03 | 13.35 | 0.68 |
| 48 | 30.71 | 34.66 | 32.68 | 1.97 |
| 72 | 51.41 | 54.10 | 52.75 | 1.35 |

| #17-03 *B. longum* R-175 | | | | |
|---|---|---|---|---|
| time (h) | run 1 | run 2 | average | range |
| 0 | 0.00 | 0.00 | 0.00 | 0.00 |
| 24 | 12.82 | 13.86 | 13.34 | 0.52 |
| 48 | 29.71 | 34.52 | 32.11 | 2.41 |
| 72 | 53.08 | 52.72 | 52.90 | 0.18 |

| #18-03 Control | | | | |
|---|---|---|---|---|
| time (h) | run 1 | run 2 | average | range |
| 0 | 0.00 | 0.00 | 0.00 | 0.00 |
| 24 | 10.90 | 11.81 | 11.36 | 0.45 |
| 48 | 30.97 | 34.32 | 32.65 | 1.68 |
| 72 | 49.83 | 53.85 | 51.84 | 2.01 |

14-03 = Example 3 formula;
15-03 = *L. helveticus* R-52;
16-03 = *L. plantarum* R-1012;
17-03 = *B. longum* R-175;
18-03 = Control In the TIM-2 study, the cumulative production of lactate in mmol for runs in which the individual strains were added (#15-03 to #17-03), were similar to the control (#18-03). However, it was surprisingly found that in the TIM-2 runs in which the formula of Example 3 was added (#14-03), lactate production was much higher. This high lactate production for the formula of Example 3 indicates fast fermentation. Although we do not wish to be bound by theory, this surprising result is likely to be due to the excipient material which is part of the formula of Example 3, for example the fructose and inulin. Furthermore, the proportion of D- to L-lactate in the runs in which the individual strains were added were similar to the control, but the runs in which the formula of Example 3 was added surprisingly produced a much higher proportion of the more beneficial L-lactate than the control.

The toxic metabolites BCFA (iso-butyrate and iso-valerate) and ammonia are metabolites produced from protein fermentation. BCFA were produced in small amounts in every run. This is expected as there is sufficient carbohydrate present in the system to prevent protein fermentation. The control (variable #18-03) gave the highest BCFA production (3.08 mmol). The variables with the individual strains (#15-03, #16-03 and #17-03) gave similar, but slightly lower BCFA production compared to the control. The formula of Example 3 (#14-03) gave lowest BCFA production, which presumably is the effect of the excipient matrix.

The amount of ammonia produced was similar for the individual strains compared to the control. For the formula of Example 3, total ammonia production after 72 hours was lowest, which corresponds with the low BCFA production and high lactate production which was found for this formula.

The formula of Example 3 also appears to have had some positive influence on the metabolic activity of the microbiota. To determine whether the tested Wyeth materials had an effect on the composition of the microbiota, the TNO I-Chip platform was used. The TNO I-Chip contains roughly 350 probes, some for group-level detection (e.g., total bifidobacteria), and some for detection of individual species (e.g., *Bifidobacterium longum*). The microbiota composition was measured at the beginning (t0) and the end (t72) of the TIM-2 runs. The change over time was compared to the change over time in microbiota composition of the control variable (#18-03). The *B. longum* R-175 probe showed a 10-fold increase of the signal of that probe for the formula of Example 3 (#14-03) and a 20-fold increase for the *B. longum* run (#17-03).

What is claimed:

1. A probiotic composition for oral administration, comprising:
   a) at least about 50 billion CFU/g *Bifidobacterium longum* R175;
   b) at least about 150 billion CFU/g *Lactobacillus helveticus* R52;
   c) at least about 150 billion CFU/g *Lactobacillus plantarum* R1012;
   d) one or more prebiotic components selected from inulin, fructose, fructooligosaccharides and mixtures thereof;
   e) lactoferrin
   f) one or more metal salts selected from the group consisting of magnesium gluconate, potassium citrate, copper citrate and zinc gluconate;
   g) optionally glutathione; and
   h) one or more excipients.

2. A probiotic composition for oral administration, comprising (a) probiotics in an amount of at least about: *Bifidobacterium longum* 50 billion CFU/g; *Lactobacillus helveticus* 150 billion CFU/g; and *Lactobacillus plantarum* 150 billion CFU/g, (b) one or more prebiotic components selected from inulin, fructose, fructooligosaccharides and mixtures thereof, (c) lactoferrin, (d) one or more metal salts selected from magnesium gluconate, potassium citrate, zinc gluconate, and copper citrate, (e) optional glutathione and (f) excipients.

* * * * *